US006242016B1

(12) United States Patent
Mehnert et al.

(10) Patent No.: US 6,242,016 B1
(45) Date of Patent: *Jun. 5, 2001

(54) RAPID METHOD FOR MANUFACTURE OF GRATED PARMESAN CHEESE

(75) Inventors: David Webb Mehnert; James William Moran, both of Antioch; Gary W. Trecker, Lake Zurich, all of IL (US)

(73) Assignee: Kraft Foods, Inc., Northfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/365,346

(22) Filed: Jul. 30, 1999

(51) Int. Cl.[7] .................................................... A23C 9/12
(52) U.S. Cl. ................................ 426/36; 426/34; 426/35; 426/38; 426/40; 426/582
(58) Field of Search .................................. 426/34, 36, 35, 426/38, 40, 580, 582

(56) References Cited

U.S. PATENT DOCUMENTS

| 3,899,596 | * | 8/1975 | Stenne | 426/40 |
|---|---|---|---|---|
| 3,914,435 | * | 10/1975 | Maubois et al. | 426/40 |
| 3,988,481 | | 10/1976 | Coulter et al. | 426/40 |
| 4,244,971 | * | 1/1981 | Wargel et al. | 426/35 |
| 4,401,679 | * | 8/1983 | Rubin et al. | 426/36 |
| 4,820,530 | | 4/1989 | Moran et al. | 426/40 |
| 4,942,052 | | 7/1990 | Posdal | 426/512 |
| 4,960,605 | * | 10/1990 | Trecker et al. | 426/582 |

FOREIGN PATENT DOCUMENTS

82/01806 6/1982 (WO).

OTHER PUBLICATIONS

Carlson, A., "The Enzymatic Coagulation of Milk," Thesis –Published 1982, University of Wisconsin.*
Ernstrom, "Cheese Base for Processing a High–Yield Product Form Whole Milk by Ultrafiltration", *J. of Dairy Science* Vol. 63, pp228–234 (1980).

* cited by examiner

*Primary Examiner*—Leslie Wong
(74) *Attorney, Agent, or Firm*—Fitch, Even, Tabin & Flannery

(57) ABSTRACT

In accordance with the method of the present invention, dried grated Parmesan cheese particles are manufactured from milk. The fat level of the milk is standardized to about 2.0 percent. The milk is subjected to membrane processing by ultrafiltration and diafiltration to provide a retentate. The retentate is then fermented with a combination of lactic acid cultures, a flavor culture, and a lipase enzyme. The fermentation is carried out at a temperature between about 90 and about 120° F. The fermented retentate is then evaporated to a solids level desired in the finished dry grated Parmesan cheese, which is generally in the range of from about 18 to about 24 percent moisture. A clotting agent is added to the fermented retentate immediately before the initiation of the evaporation step. Evaporation is preferably carried out in a drum drier under quiescent conditions. The Parmesan cheese is removed from the drum drier and is transferred to a disintegrator, such as a Fitz mill, to provide a grated Parmesan cheese product. The grated Parmesan cheese may be then blended with an anticaking material and an antimycotic material prior to packaging for consumer use without further aging or curing.

20 Claims, 2 Drawing Sheets

RAPID METHOD FOR MANUFACTURE OF GRATED PARMESAN CHEESE

BACKGROUND OF THE INVENTION

The present invention is directed to a rapid method for the manufacture of grated hard cheese. More particularly, the method of the present invention provides grated hard cheese, especially grated Parmesan cheese, by a rapid and efficient method.

FIELD OF THE INVENTION

Parmesan cheese is the name in common use for a group of very hard cheeses which are customarily used in a grated form. Included in the group are Parmigiano, Reggiano, Lodigiano, Lombardi, Emiliano, Veneto, and Baggozo. They differ in size, shape, and fat content. Also, there are some differences in methods of manufacture. Fully cured Parmesan cheese is very hard and keeps almost indefinitely. It can be grated easily and is commonly used as grated cheese on salads, soups, and pasta. In the United States, Parmesan cheese is usually cured for ten months. Normally, the moisture level of the cured cheese is between 30 and 32 percent and the fat level is between 22 and 32 percent.

It is known to produce a grated Parmesan cheese which is sold in containers for direct use on salads, soups, pasta, and the like. The grated Parmesan cheese usually available in the marketplace is dried, after curing, to a moisture level of from about 12 and 18 percent. At this moisture level, there is little problem of clumping or agglomeration of the grated cheese product. U.S. Pat. No. 4,960,605 to Trecker et al. describes a method for making a grated Parmesan cheese which has a higher moisture level (i.e., about 19 to about 24 percent). In accordance with this patent, disodium phosphate is added to grated Parmesan cheese particles having a moisture content when packaged of about 19 to about 24 percent. In the method of Trecker et al., conventional fill moisture Parmesan cheese (i.e., aged for at least 10 months and having a moisture content of about 30 to 32 percent) is first shredded. The Parmesan shreds are transported with the aid of a conveyor to a surge bin and are discharged from the surge bin through an auger conveyor which transports the cheese to a hammer-mill disintegrator to provide a grated cheese. The grated Parmesan cheese is fed directly from the hammer-mill disintegrator to a fluid bed drier. The finished grated Parmesan is discharged from the drier at about 22 percent moisture.

The manufacture of cheeses or cheese base materials from milk through preparation of a retentate by removal of salts, lactose, and water has been taught in various patents and literature references. For example, Coulter et al., U.S. Pat. No. 3,988,481, teaches the preparation of cheese from milk which has been de-lactosed and de-watered by a process involving molecular sieving a standardized milk to substantially separate and remove lactose and water-soluble minerals from the milk to render the milk substantially sugar-free, and adding a curd-forming agent to produce curd. The resulting curd is subjected to conventional handling without substantial syneresis to produce a cheese, and molded to a desired form.

Stenne, U.S. Pat. No. 3,899,596, discloses a process for the production of cheese which comprises treating milk by ultrafiltration to obtain a product having at least some of the protein constituents of the milk, renneting the liquid product after inoculation with suitable ferments, and introducing a batch of the renneted liquid into a vertical chamber in which it is left to coagulate. The coagulum is cut into slabs which provide the end product cheese.

Maubois et al., U.S. Pat. No. 3,914,435, teaches a manufacturing process whereby cheese is prepared from heat-treated milk without a conventional drainage step. This process involves ultrafiltering of the milk to produce a concentrate having essentially the composition of cheese produced by conventional whey draining processes. The process allows the milk, after ultrafiltration, to be heat-treated without making the milk more difficult to coagulate with rennet, which difficulty normally occurs when milk is heated to high temperatures.

Wargel et al., U.S. Pat. No. 4,244,971, teaches the manufacture of cheeses and process cheese from ultrafiltered milk. Rubin et al., U.S. Pat. No. 4,401,679, discloses a process for preparing cheese base by concentrating milk through ultrafiltration, combined with diafiltration and evaporation, wherein the retentate from the ultrafiltration is inoculated with a lactic acid culture before evaporation. After evaporation, acidification proceeds to completion during and after packaging.

Further, cheese base material has been taught by evaporating moisture from retentate under turbulent conditions to provide a lower moisture condition. Such a process is described in an article by Ernstrom et al., entitled "Cheese Base for Processing: A High-yield Product from Whole Milk by Ultrafiltration," *Journal of Dairy Science*, Volume 63, pp. 228–234 (1980). The article teaches a process wherein whole milk of normal pH, or acidified to a pH of 5.7, is concentrated by ultrafiltration to about 40 percent of the original milk weight and diafiltered at constant volume until a desired ratio of lactose to buffer capacity is established. The retentate is further concentrated by ultrafiltration to 20 percent of the original milk weight. The retentate is then inoculated with cheese starter and incubated to completely ferment the residual lactose. The pH is controlled by adjusting the level of lactose from the diafiltration step of the process. The product is further concentrated in a swept-surface vacuum-pan evaporator or a Luwa evaporator. It is pointed out that the use of a batch evaporator is necessitated when the retentate, upon fermentation, curdles or coagulates, since such a product cannot be readily processed in any continuous-flow evaporator.

It is also known to add salt during fermentation to prevent coagulation. See, e.g., *LeLait,* November–December, 539–540 (1974). Further, it has been disclosed that salt in the retentate may facilitate evaporation. PCT WO82/01806 (Jun. 10, 1982).

However, the prior art teaches that addition of rennet or other coagulating enzymes to high-solids milk systems causes rapid coagulation, a condition to be avoided during evaporation, as indicated above, since the evaporation is highly inefficient after coagulation occurs. On the other hand, the presence of coagulating enzymes may be desired, particularly in higher-solids cheese, to provide the conventional presence of para kappa casein. The kinetics of enzymatic coagulation of milk is disclosed by Alfred Carlson, in a thesis published in 1982, at the University of Wisconsin, entitled "The Kinetics of Enzymatic Coagulation of Milk".

In the conventional cheese-making with rennet, the macro peptides formed by rennet action are lost in the whey with consequently reduction in yield and loss of nutritious milk protein material. Accordingly, it would be desirable to enjoy the benefit of rennet action while avoiding whey removal with consequent loss of macro peptides.

Further, prior art methods for making cheese base materials at higher-solids with evaporation, in which evaporation is effected with high turbulence or the cheese base material is recovered with substantial working after evaporation, has resulted in destabilization of the higher-solids cheese base material, thereby providing body and texture unlike various cheeses. This destabilization is particularly noticeable at total solids in excess of about 60 to 62 percent (e.g., a cheese such as cheddar cheese) but is also present at solids as low as 55 percent. Accordingly, cheese base materials heretofore produced by evaporating retentates to a total solids in excess of 60 percent have not provided the typical body and texture characteristics of high-solids cheeses.

In addition, the use of high turbulence throughout evaporation or working after evaporation does not provide a curd-like product. Prior art methods for making cheese from retentates with evaporation techniques do not disclose a method for making a curd-like product.

The prior art teaches many different steps in respect to the manufacture of cheeses and cheese base materials from milk retentates. Evaporation of milk retentates is a previously known technique, but the resultant product does not have curd character, nor does it convert to a product having the body and texture of cheese. Also, much of the prior art is directed toward the manufacture of higher moisture or soft cheeses, and it has not been directed toward the production of high-solids cheeses from retentates by means of evaporation of retentates. Using turbulence at higher-solids levels (i.e., above 55 percent total solids) results in product destablization and the exudation of fat, thereby forming a high-solids product (i.e., above 60 percent total solids) lacking the desired characteristic cheese body and texture. If the moisture levels are high enough (i.e., about 50 to about 55 percent moisture), fat exudation can be avoided and the body and texture of soft cheeses can be provided.

While the addition of milk clotting or coagulating enzymes to retentates has been known, such addition has generally been made with concurrent formation of a coagulum which cannot be readily subjected to evaporation, and which is destroyed by turbulence and/or working.

Many of the problems associated with the manufacture of curd and cheese from a milk retentate were resolved by the method taught in U.S. Pat. No. 4,820,540 to Moran et al. In the Moran et al. method, a milk retentate is fermented with conventional cheese cultures normally used in manufacture of American-type cheeses (e.g., *Streptococcus lactis* and *S. cremoris*). The fermentation is controlled to prevent coagulation by limiting acid production to provide a pH of from about 4.9 to about 5.6 (i.e., above the isoelectric pH of the casein in the retentate). A coagulating enzyme is added immediately prior to evaporation. The fermented retentate is then dried quiescently by applying the retentate to a vacuum drum dryer. After drying to a total solids level of about 55 percent, a cheese curd is provided which can be used in process cheese or textured to yield a cheese.

SUMMARY OF THE INVENTION

In accordance with the method of the present invention, dried grated Parmesan cheese particles are manufactured from milk. The fat level of the milk is standardized to about 2.0 percent. The standardized milk is treated, preferably by membrane processing using ultrafiltration and diafiltration, to provide a retentate having a moisture content of about 50 to about 83 percent, a salts level of about 1.0 to about 2.5 percent, and a lactose level of less than about 2.0 percent. The retentate is then fermented with a combination of lactic acid cultures, a flavor culture, and a flavor enzyme. The fermentation is carried out at a temperature between about 90 and about 120° F. After adding a coagulating enzyme, the fermented retentate is then evaporated to solids and moisture levels desired in the finished dry grated Parmesan cheese (i.e., generally about 18 to about 24 percent moisture). It is important that the coagulating enzyme is added immediately prior to the evaporation step. The dried Parmesan cheese is removed from the drum drier and is transferred directly to a disintegrator, such as a Fitz mill, to provide a grated Parmesan cheese product. The grated Parmesan cheese may be then blended with anticaking materials and/or antimycotic materials prior to packaging for consumer use without further aging.

DETAILED DESCRIPTION OF THE INVENTION

Figure 2:
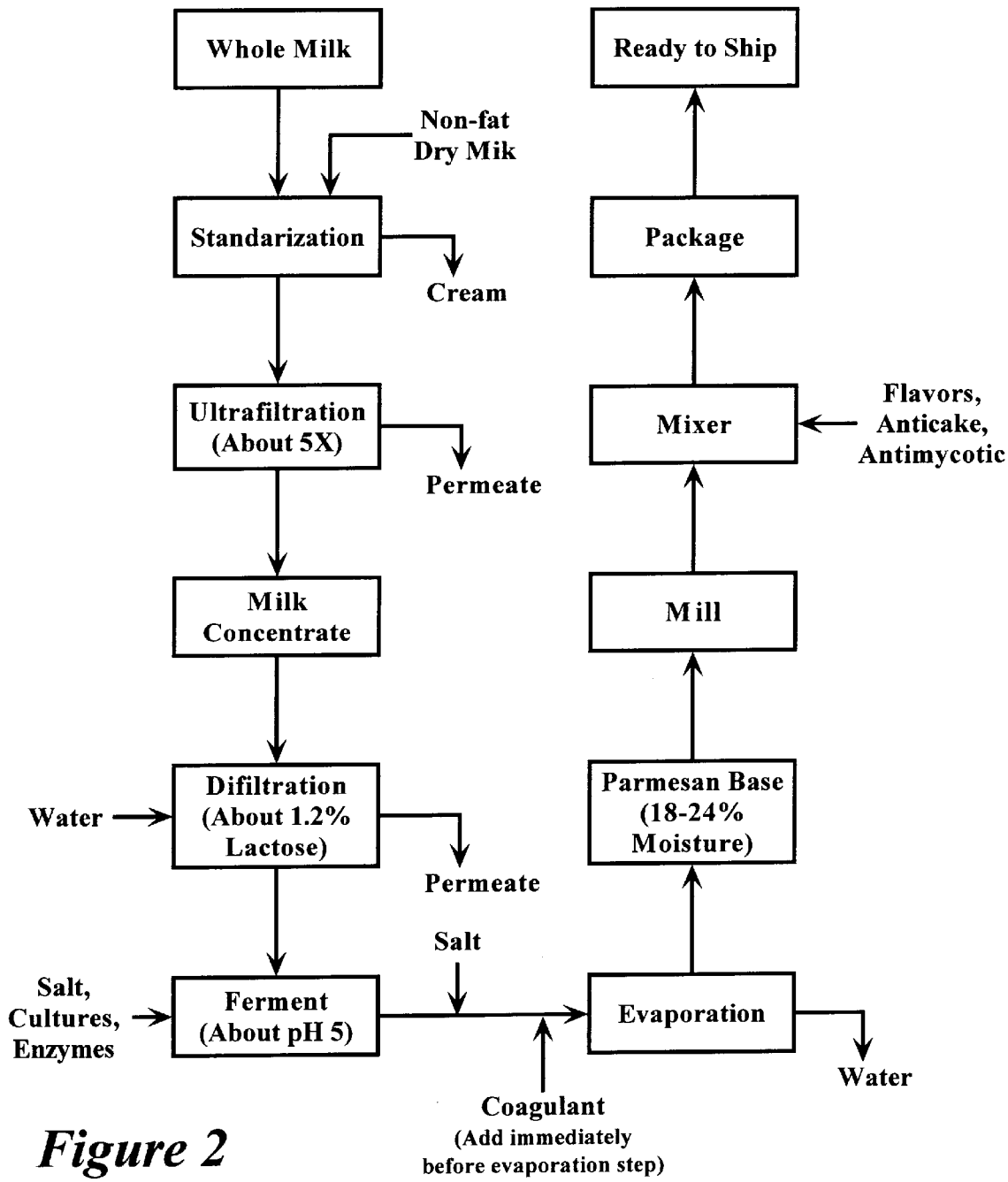
FIG. 2 is a flow diagram illustrated the improved method of the present invention for the production of Parmesan Cheese.

In accordance with the invention and as more particularly illustrated in FIG. 2, milk is standardized by adding non-fat dry milk or skim milk and/or by adding or removing cream as appropriate. Generally, the standardized milk contains about 2.9 to about 3.5 percent protein and about 1.8 to about 2.2 percent fat, and, more preferably about 3.0 to about 3.4 percent protein and about 1.9 to about 2.1 percent fat. The standardized milk is then treated to provide a retentate having between about 50 and about 83 percent moisture; between about 0.7 and about 2.5 percent salts; and less than about 2.0 percent lactose. The retentate from whole milk will preferably have a moisture between about 50 and about 70 percent, a salts level between about 1.0 and about 2.5 percent, and a lactose level below about 1.8 percent. Retentates from skim milk will preferably have a moisture between about 78 and about 83 percent, a salts level between about 0.7 and about 1.9 percent, and lactose level below about 1.5 percent.

Various techniques are known in the art for achieving the indicated retentates, including, for example, ultrafiltration with or without diafiltration. Commercial equipment is marketed and available for the preparation of such retentates, and such equipment is in present use in the cheese industry. The operation of such apparatus is believed to be within the skill of the art. Preferably, in the practice of the invention, the milk is treated by ultrafiltration and diafiltration to provide the desired level of constituents in the retentate.

Raw whole milk is stored at 40° F. and standardized to provide a protein to fat ratio of about 1.4 to about 1.7 and a total fat content of from about 1.8 to about 2.2 percent, preferably about 2.0 percent. Standardization is achieved by the addition of skim milk and/or the removal of cream. If desired, skim milk can be used as the starting material; in that case, however, cream would be added to standardize to the desired protein to fat ratio. The standardized milk is then pasteurized at 163° F. for 16 seconds, then cooled to 40° F. The milk is warmed to a temperature of from about 110 to about 130° F. The milk is then subjected to ultrafiltration to achieve a concentration of from about 25 to about 35 percent solids. The milk is then diafiltered at a water to concentrate ratio of about 1.5 to 1.0. After diafiltration, ultrafiltration is continued until about 5 fold concentration is achieved. The ultrafiltration/diafiltration process is conducted to achieve a lactose level of from about 1.2 to about 1.4 percent and to provide milk salts or ash levels of from about 1.6 to about 2.2 percent. The retentate has from about 30 to about 40 percent total solids and from about 60 to about 70 percent moisture.

The concentrated retentate is then heat treated at a temperature of from about 150 to about 175° F. for a period of from about 10 to about 60 seconds and is then cooled to a temperature of from about 60 to about 75° F. until needed for fermentation. The maximum storage time at this temperature is from about 12 to about 20 hours. At lower storage temperatures, viscosity increases to unacceptable levels for the process. Should the storage temperature of the concentrated retentate fall below about 60° F., it should be raised to about 60 to about 75° F. to reduce the viscosity before proceeding with the process. The retentate is appears to be microbiologically stable under these conditions.

The concentrated retentate is warmed to a temperature of from about 100° F. to about 120° F. for fermentation. Sodium chloride is added at a level of from about 0.1 to about 1.5 percent. A lactic acid producing culture selected from the group consisting of *Lactococcus lactis* and *Streptococcus lactis* (preferably subspecies *thermophilus*), and a Parmesan cheese flavor culture selected from the group consisting of *Lactobacillus helveticus* and *Lactobacillus casei* are used in the fermentation. The lactic acid producing culture is generally added at a level of about 1.25 to about 2.5 ml active culture per 75 pounds of concentrated retentate; the Parmesan cheese flavor culture is generally added at a level of about 1.5 to about 2.5 ml active culture per 75 pounds concentrated retentate. Additionally a blend of calf, kid, and lamb pregastric esterase enzyme or microbial lipase enzyme is added at a level of 0.1 gm active enzyme to per 75 pounds of concentrated retentate. As those skilled in the art will realize, higher or lower amounts of these enzymes can be used.

The fermentation is carried out at a temperature of from about 70 to about 120° F. for a period of from about 12 to about 20 hours and until the fermented retentate reaches a pH of about 5.1. The fermented retentate is cooled to a temperature of from about 65 to about 90° F. prior to evaporation. After cooling, sodium chloride is added at a rate to yield a salt level in the finished dried product of from about 3.75 to about 4.75.

A milk clotting enzyme, such as modified *Mucor meihei* enzyme, is added to the fermented retentate under carefully controlled conditions. Other milk clotting enzymes can be used. Generally the amount of the milk clotting enzyme added is about 0.0015 to about 0.0025 percent. More specifically, the milk clotting enzyme is added just before or immediately before the evaporation step (i.e., within about 60 seconds, preferably within about 20 seconds, and most preferably within about 10 seconds, of the initiation of the evaporation step). Thus, once the milk clotting enzyme is added, evaporation must be started immediately. Moreover, the milk clotting enzyme must be added before evaporation begins.

The fermented retentate is then concentrated by evaporation or drying using conventional techniques and equipment such as, for example, drum drying, vacuum drum drying, freeze drying, or the like. Preferably, evaporation is carried out under quiescent conditions from a heated surface. The preferred heated surface consists of a pair of counter-rotating drums whose surface is maintained at a temperature of from about 65 to about 120° F. The fermented retentate is compressed at the nip of the drums and dried cheese sheet is formed on the bottom surface of each drum. Doctor blades are provided at the lower portion of the drums to remove the dried cheese from the drums. The drum surfaces, as well as the feed systems for spreading the fermented retentate thereon and the doctor blades, are maintained in a relatively high vacuum environment (approximately 0.04 atmospheres) to reduce the boiling point of the liquid retentate, thereby providing the desired evaporation with significantly lower cheese temperature (below a temperature of from about 80 to about 90° F.) than would otherwise be possible.

Figure 1:
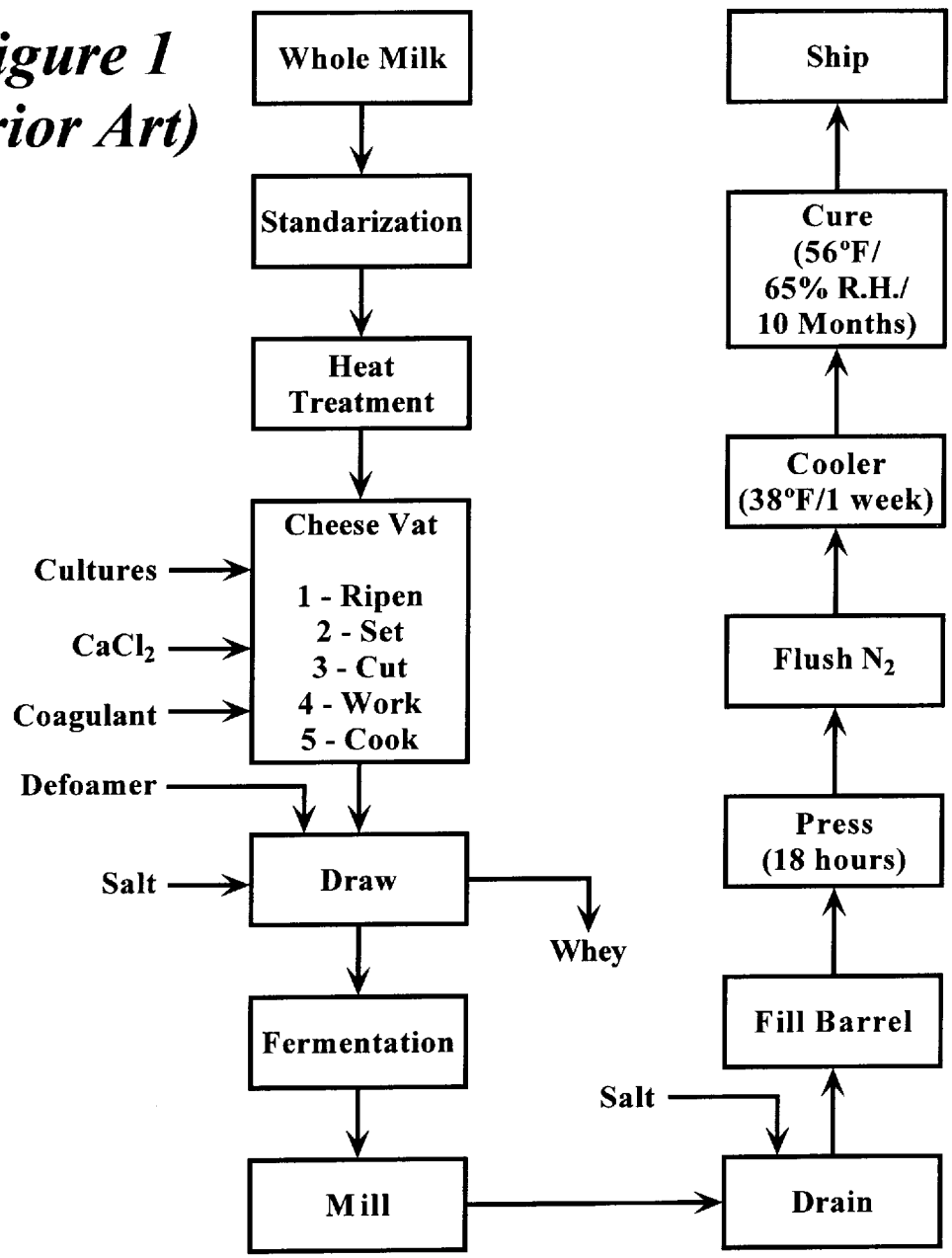
FIG. 1 is a flow diagram illustrating conventional methods for the production of grated Parmesan Cheese.

The dried Parmesan cheese removed from the drums is collected in a space below the drums and preferably removed by use of two sliding panels in order to maintain vacuum in the area of the feed and drums. The dried cheese is reduced in size by use of a Fitz mill to provide a finished grated Parmesan cheese product having a particle size of from about 1/32 to about 1/8 inch. The grated Parmesan cheese product may be combined with anticake and antimycotic materials and blended in a tumble drum before being packaged by conventional packaging equipment. Using the process of this invention, the Parmesan cheese is ready for immediate shipment to grocery stores (or other outlets). Thus, using the method of the present invention, it is not necessary to cure the resulting cheese product for up to ten months are required by the prior process. The advantages of the present invention can be illustrated by a comparison of FIG. 1 which illustrates the general prior art process for preparing Parmesan cheese and FIG. 2 which illustrate the present inventive process. Not only is the curing step (as well as the one week cooling step) in the prior art process eliminated, the process of the present invention is significantly simpler. Although the Parmesan cheese produced by the method of this invention has excellent flavor characteristics, additional flavors, both in liquid and solid form, can be added to the final product if desired.

In the process of the invention, it is important that coagulation is avoided prior to drying or evaporation step. Thus, milk clotting agent is added to the fermented curd less than 60 seconds, preferably less than about 20 seconds, and most preferably less than about 10 seconds, prior to transferring the fermented curd to the drum drier. Thus, coagulation in the present invention only takes place in the evaporation or drying unit.

The practice of the invention will be more clearly understood by reference to the following example. This example is intended to illustrate the invention and not to limit it. All percentages used herein are by weight, unless otherwise indicated.

EXAMPLE

Raw whole milk is stored at 40° F. and is standardized to a desired protein to fat ratio of about 1.6 and a total fat content of 2.0 percent. The standardized milk is then pasteurized at 163° F. for 16 seconds, then cooled to 40° F. The standardized milk is warmed to about 120° F. and is then subjected to ultrafiltration to achieve a concentration of 30 percent total solids. The ultrafiltered milk is then diafiltered. The diafiltration is run at about 1.5 to 1.0 (water to concentrate). After diafiltration, ultrafiltration is continued until about a 5.0 fold concentration is achieved. The ultrafiltration/diafiltration process is conducted to achieve a lactose level of about 1.4 percent and to provide milk salts or ash level of about 1.9 percent. The retentate has about 35 percent total solids and about 65 percent moisture.

The concentrated retentate is then heat treated at 165° F. for 16 seconds and cooled to 60° F. until needed for fermentation. The concentrated retentate is warmed to 110° F. for fermentation. A salt (sodium chloride) solution is added at a level of 0.4 percent (by weight of salt to retentate). Direct vat set cultures (DVS) *Lactococcus lactis, Streptococcus lactis* subspecies *thermophilus, Lactobacillus helveticus,* and *Lactobacillus casei* culture are used in the fermentation. About 1.25 to 2.5 ml of the DVS culture (Charles Hansen Laboratory, Milwaukee, Wis.) and about 2.0 ml of *Lactobacillus casei* (frozen concentrate) were added to 75 pounds of concentrated retentate. Additionally a blend of calf, kid, and lamb pregastric esterase enzyme is added at a rate of 0.1 gm active enzyme (SKW Biosystems, Madison, Wis.) to 75 pounds of concentrated retentate.

The fermentation is carried out at 110° F. until the pH of the fermented retentate reaches 5.1 (generally within about 16 hours). The fermented retentate is cooled to 72° F. prior to initiation of the evaporation step. After cooling, salt (sodium chloride) is added at a rate to yield a salt level in the finished dried product of 4.25 percent. A milk clotting enzyme, a *Mucor meihei* enzyme (Marzyme Supreme form Rhodia Ingredients, Madison, Wis.), is added to the fermented retentate about 10 seconds prior to initiation of the evaporation step. The desired level of salt should be added before or with the addition of the milk clotting agent.

The resulting fermented retentate, at a solids level of about 36 percent, is then concentrated by spreading on a heated surface such that the moisture is evaporated from the retentate under quiescent conditions. The preferred heated surface consists of a pair of horizontally-mounted counter-rotating drums. Generally, the speed and diameter of the drums, the level of vacuum, and the temperature can be adjusted as needed to maintain the desired quiescent conditions. The fermented retentate is compressed at the nip of the drums and dried cheese sheet is formed on the bottom surface of each drum. Doctor blades are provided at the lower portion of the drums to remove the dried cheese from the drums. The drum surfaces, as well as the feed systems for spreading the fermented retentate thereon and doctor blades, are maintained in a relatively high vacuum environment (approximately 0.04 atmospheres) to reduce the boiling point of the liquid retentate. Using this vacuum system, the desired evaporation is possible at significantly lower cheese temperature (e.g, below about 85° F.).

The dried Parmesan cheese removed from drums is collected in a space below the drums and removed by use of two sliding panels in order to maintain vacuum in the area of the feed and drums. The dried cheese is reduced in size by use of a Fitz mill, combined with anticake and antimycotic materials, mixed in a tumble drum, and then packaged by conventional packaging equipment. When blending is complete, the finished product can packaged using conventional packaging techniques and equipment. Preferably, the finished product is packaged under an inert atmosphere. The finished product is ready for immediate shipment to retail outlets and/or consumption by consumers. In other words, no aging or curing period is required. In conventionally prepared Parmesan cheese, an aging or curing time of up to 10 months is normally required.

What is claimed is:

1. A process for the rapid manufacture of grated Parmesan cheese from milk, said process comprising the steps of:
   (a) removing salt and lactose from the milk to provide a retentate having between about 50 and 83 percent moisture, between about 0.7 and about 2.5 percent salt, and less than about 3.0 percent lactose;
   (b) adding a lactic acid producing cultures, a Parmesan cheese flavor culture, a lipase enzyme, and salt to the retentate and fermenting the retentate at a temperature of from about 70 to about 120° F. until the fermented retentate obtains a pH of between about 4.8 and about 5.4;
   (c) adding salt to the fermented retentate at a level sufficient to provide from about 3.75 to about 5.0 percent salt in the Parmesan cheese;
   (d) adding a milk clotting enzyme to the fermented retentate of step (c) and then immediately beginning evaporation of moisture from the fermented retentate to provide the Parmesan cheese with a moisture content of from about 18 to about 24 percent; and
   (e) transferring the Parmesan cheese directly from the evaporation step to a disintegrator to provided a grated Parmesan cheese,
   wherein the Parmesan cheese and the grated Parmesan cheese do not require curing.

2. The process as defined in claim 1, wherein the milk is standardized to about 2.9 to about 3.5 percent protein and about 1.8 to about 2.2 percent fat prior to removing salt and lactose in step (a).

3. The process as defined in claim 1, wherein the milk clotting enzyme is added to the fermented retentate no more than about 20 seconds prior to beginning evaporation.

4. The process as defined in claim 2, wherein the milk clotting enzyme is added to the fermented retentate no more than about 20 seconds prior to beginning evaporation.

5. The process as defined in claim 3, wherein the lactic acid producing culture is selected from the group consisting of *Lactococcus lactis* and *Streptococcus lactis*.

6. The process as defined in claim 4, wherein the lactic acid producing culture is selected from the group consisting of *Lactococcus lactis* and *Streptococcus lactis*.

7. The process as defined in claim 3, wherein the Parmesan cheese flavor culture is selected from the group consisting of *Lactobacillus helveticus* and *Lactobacillus casei*.

8. The process as defined in claim 4, wherein the Parmesan cheese flavor culture is selected from the group consisting of *Lactobacillus helveticus* and *Lactobacillus casei*.

9. The process as defined in claim 3, wherein the lipase enzyme is a blend of calf, kid, and lamb pregastric esterase.

10. The process as defined in claim 4, wherein the lipase enzyme is a blend of calf, kid, and lamb pregastric esterase.

11. The process as defined in claim 3, wherein the retentate from step (a) is heat treated at a temperature of about 150 to about 175° F. for a period of time of about 10 to about 60 seconds and is then cooled to a temperature of about 60 to about 75° F. until required for use in step (b).

12. The process as defined in claim 4, wherein the retentate from step (a) is heat treated at a temperature of about 150 to about 175° F. for a period of time of about 10 to about 60 seconds and is then cooled to a temperature of about 60 to about 75° F. until required for use in step (b).

13. The process as defined in claim 3, wherein the evaporation is effected by spreading the fermented retentate from step (c) on a drum dryer prior to coagulation of the spread fermented retentate and wherein the drum dryer is maintained under vacuum.

14. The process as defined in claim 4, wherein the evaporation is effected by spreading the fermented retentate from step (c) on a drum dryer prior to coagulation of the spread fermented retentate and wherein the drum dryer is maintained under vacuum.

15. The process as defined in claim 3, wherein the milk clotting enzyme is added to the fermented retentate no more than about 10 seconds prior to beginning evaporation, and wherein the evaporation is effected by spreading the fermented retentate on a heated surface under quiescent conditions.

16. The process as defined in claim 4, wherein the milk clotting enzyme is added to the fermented retentate no more than about 10 seconds prior to beginning evaporation, and wherein the evaporation is effected by spreading the fermented retentate on a heated surface under quiescent conditions.

17. The process as defined in claim 15, wherein the heated surface is a drum dryer and the heated surface is maintained at a temperature of about 70° F. to about 120° F.

18. The process as defined in claim 16, wherein the heated surface is a drum dryer and the heated surface is maintained at a temperature of about 70° F. to about 120° F.

19. The process as defined in claim 3, wherein the fermentation in step (b) is carried out over a period of about 12 to about 20 hours.

20. The process as defined in claim 4, wherein the fermentation in step (b) is carried out over a period of about 12 to about 20 hours.

* * * * *